(12) United States Patent
Karge et al.

(10) Patent No.: US 8,252,927 B2
(45) Date of Patent: Aug. 28, 2012

(54) SYNTHESIS OF SUBSTITUTED 4-AMINO-PYRIMIDINES

(75) Inventors: Reinhard Karge, Staufen (DE); Ulla Letinois, Saint-Louis (FR); Gerhard Shiefer, Buggingen (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/055,579

(22) PCT Filed: Jul. 22, 2009

(86) PCT No.: PCT/EP2009/059415
§ 371 (c)(1),
(2), (4) Date: Apr. 7, 2011

(87) PCT Pub. No.: WO2010/010113
PCT Pub. Date: Jan. 28, 2010

(65) Prior Publication Data
US 2011/0178300 A1    Jul. 21, 2011

(30) Foreign Application Priority Data

Jul. 22, 2008   (EP) .................................... 08013151

(51) Int. Cl.
C07D 239/02   (2006.01)
(52) U.S. Cl. ....................................................... 544/326
(58) Field of Classification Search .................... 544/326
See application file for complete search history.

(56) References Cited

U.S. PATENT DOCUMENTS 4,226,799 A * 10/1980 Bewert et al. ................. 558/395

FOREIGN PATENT DOCUMENTS

| DE | 3511273 A1 * | 10/1986 |
| EP | 0 001 760 | 5/1979 |
| EP | 0 172 515 | 2/1986 |
| WO | WO 0006569 A1 * | 2/2000 |
| WO | WO 2006/079504 | 8/2006 |
| WO | WO 2007/104442 | 9/2007 |

OTHER PUBLICATIONS

International Search Report for PCT/EP2009/059415, mailed Oct. 28, 2009.
Elvers, B. et al.,"Ullmann's Encyclopedia of Industrial Chemistry; Passage", Ullmann's Encyclopedia of Industrial Chemistry, Thorium and Thorium Compounds to Vitamins, vol. A27, (Jan. 1, 1996), pp. 515-517.

Bacher, E. et al., "1-Acceptorsubstituierte Vinamidiniumsalze: Stabilitaet Und Reaktivitaet 1-Acceptor Substituted Vinamidinium Salts: Stability and Reactivity", Zeitschrift Fur Naturforschung, Teil B: Anorganische Chemie, Organische Chemie, Verlag Der Zeitschrift Fur Naturforschung, vol. 44, No. 7, (Jul. 1, 1989), pp. 839-849.
Mohrle, H. et al., "Aminomethylierung vinyloger Cyanamide", Pharmazie, vol. 39, (1984), pp. 384-386.
Takamizywa, A. et al., "Studies on the Pyrmidine Derivatives, XXIX, Reactions of 3-Ethoxy-2-methoxymethylenepropionitrile and 3-Ethoxy-2-ethoxymethylpropionitrile with Urea and Thiourea Derivatives", Journal of Organic Chemistry, vol. 29, (1964), pp. 1740-1743.

* cited by examiner

*Primary Examiner* — James O Wilson
*Assistant Examiner* — Alexander R Pagano
(74) *Attorney, Agent, or Firm* — Nixon & Vanderhye P.C.

(57) ABSTRACT

The present invention is directed to a process for the manufacture of compounds of formula IV wherein $R^1$ is an amino protecting group, and $R^2$ is hydrogen or $C_{1-10}$ alkyl, comprising a) reacting a compound of formula Ia, wherein $M^+$ is a cation, preferably selected from the group consisting of $Li^+$, $Na+$, $K^+$, ½ $Mg^{2+}$ and ½ $Zn_{2+}$, (formula 1a) with an ammonium salt $NH_4^+X^-$, wherein $X^-$ is an anion, preferably selected from the group consisting of chloride, bromide, sulfate and acetate, in a solvent to a compound of formula II b) reacting a compound of formula II with a nitrile $R^2$—CN in the presence of a base to a compound of formula IV. The present invention is further directed to compounds of formula II and their use for the manufacture of vitamin $B_1$.

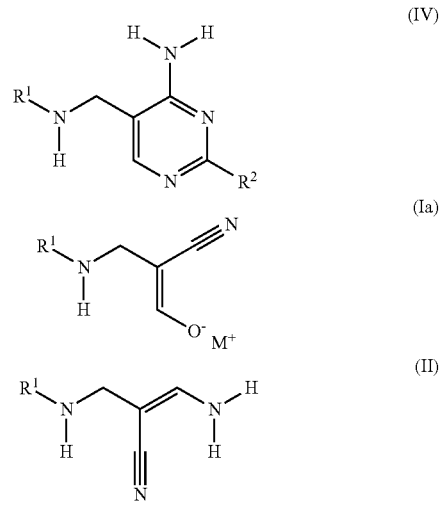

3 Claims, 2 Drawing Sheets

Vitamin B$_1$

SYNTHESIS OF SUBSTITUTED 4-AMINO-PYRIMIDINES

This application is the U.S. national phase of International Application No. PCT/EP2009/059415, filed 22 Jul. 2009, which designated the U.S. and claims priority to EP Application No. 08013151.9, filed 22 Jul. 2008.

FIELD The present invention relates to the direct transformation of an N-substituted N-(3-amino-2-cyanoallyl)amine (especially of N-(3-amino-2-cyanoallyl)formamide) to substituted 4-amino-pyrimidines. In particular it relates to a new reaction to 2-alkyl-4-amino-5-formylaminomethylpyrimidines (especially to 2-methyl-4-amino-5-formylaminomethyl-pyrimidine) by a cyclization reaction of N-substituted N-(3-amino-2-cyanoallyl)amines (especially of N-(3-amino-2-cyanoallyl)formamide) and alkylnitriles such as acetonitrile.

BACKGROUND AND SUMMARY

Importance of 4-Aminopyrimidines 4-aminopyrimidines and the aminosubstituted derivatives can be found as structural elements in several antibiotic substances, in herbicides as well as in vitamin $B_1$.

Amprolium (sold as CORID®) for example, thiamin analog, competitively inhibits the active transport of thiamin. The coccidia are 50 times as sensitive to this inhibition as is the host. It can prevent costly coccidial infection in exposed cattle and treat clinical outbreaks when they do occur. By stopping coccidia in the small intestine, CORID® prevents more damaging coccidiosis in the large intestine.

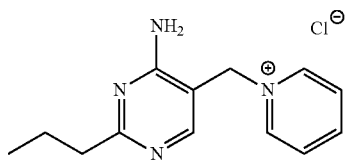

Importance of 4-Amino-5-Aminomethyl-2-Methylpyrimidine 4-amino-5-aminomethyl-2-methylpyrimidine is an important intermediate in the synthesis of vitamin $B_1$. Vitamin $B_1$ (thiamin) is used chiefly in the form of chloride hydrochloride (1) and nitrate.

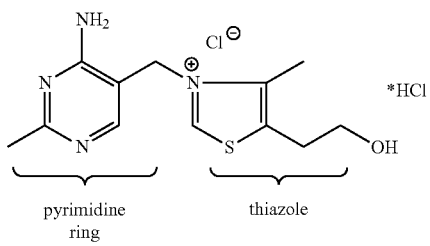

It is widespread in nature, for example 2.05 mg/100 g wheat germ, 1.3 mg/100 g in soybeans. A deficiency in vitamin $B_1$ in the human being is associated with the disease beriberi, with imbalances in carbohydrate status and deleterious effects on nerve functions. A human being needs 20-30 µg/kg body weight, which corresponds to 0.3-1.5 mg/d daily allowance. Since extraction of thiamin from natural sources would not be economically profitable, it has to be manufactured by chemical synthesis. Industrial production of vitamin $B_1$ started in 1937 by Hoffmann-La Roche in Switzerland and Merck in the United States. Commercially available forms of thiamin are the chloride hydrochloride and the mononitrate.

4-amino-5-aminomethyl-2-methylpyrimidine is a key-intermediate in the synthesis of thiamin which contains a thiazole and a pyrimidine ring. One main approach towards the synthesis of thiamin is the pyrimidine synthesis and subsequent formation of the thiazole ring attached to the pyrimidine moiety from 4-amino-5-aminomethyl-2-methylpyrimidine and 3-chloro-5-hydroxypentan-2-one, the 3-mercaptoketone or the corresponding acetates. Several procedures have been published for the synthesis of 4-amino-5-aminomethyl-2-methylpyrimidine. The building blocks are based on a C2-unit, e.g. acetamidine, and a C1-unit, usually from CO. Acrylonitrile can be used as C3-unit as a cheap starting material for the synthesis.

STATE OF THE ART

JP 39022009 and JP 39022010 describe the synthesis of 2-methyl-4-amino-5-formyl-aminomethylpyrimidine by reacting formamidine hydrochloride with sodium and ethanol to liberate the amidine followed by an addition of 2-(ethoxymethoxymethyl)-3-ethoxy-propionitrile. This procedure is disadvantageous as it necessitates an extra reaction step, the liberation of formamidine from the hydrochloride and the synthesis of the enol ethyl ether.

The UBE-Takeda procedure for over seven steps (EP-A 055 108; EP-A 279 556; DE-A 33 03 815; EP-A 124 780; EP-A 290 888; DE-A 32 22 519) includes in the first step the transformation of acrylonitrile to cyanoacetaldehyde-dimethylacetal. This step is very complex and requires major investigations because the oxidation of acrylonitrile with methyl nitrite leads to the formation of nitrous gases which have to be reoxidized to nitrite (EP-A 055 108).

The UBE-approach over 5 steps (DE-A 32 18 068, JP 58 065 262) needs two equivalents of acetamidine hydrochloride. Acetamidine hydrochloride is expensive; therefore it is disadvantageous to use two equivalents as starting material.

The 5 step procedure from BASF (EP-A 172 515) uses o-chloroaniline for the synthesis of the corresponding enamine. o-Chloroaniline is suspected to provoke cancer. The enamine is used in the following step for the cyclization with acetamidine. After the formation of 4-amino-5-aminomethyl-2-methylpyrimidine the o-chloroaniline has to be separated and re-used in a complex process.

DE-A 34 31 270 describes the use of the same technology as EP-A 172 515, specifically using o-chloroaniline as amine, which is highly carcinogenic and traces of o-chloroaniline have been found in the end-product vitamin B1.

Acrylonitrile reacts to aminopropionitrile (APN) in the presence of ammonia. APN is a commercially interesting intermediate, e.g. as it is useful as starting material for both the synthesis of vitamin $B_1$ as well as the synthesis of calcium pantothenate (see scheme 1).

The key-step in this approach is the cyclization of derivatives of α-formyl-β-formylamino-propionitrile sodium salt with acetamidine. These derivatives can be for example the enamines, acetates or methylenolethers of α-formyl-β-formylaminopropionitrile sodium salt (see for example EP-A 001 760, DE-A 28 18 156, DE-A 23 23 845). For the cyclization reaction between a derivative of α-formyl-β-formylaminopropionitrile sodium salt and acetamidine, the acetamidine has to be liberated from its hydrochloride. For this procedure commercially available acetamidine hydrochloride has to be neutralized with one equivalent of a base, usually sodium methanolate, leading to the unstable free acetamidine base and one equivalent of salt waste. The synthesis of acetamidine hydrochloride is highly corrosive and acetamidine itself is very expensive. Thus, severe drawbacks of this procedure are the formation of a salt, additional costs for the base and additional reaction steps including work-up, e.g. by filtration of the salts. The amine serves as a chemical auxiliary, upon reaction with acetamidine it is released and can be recycled, however, loss and contamination of the end-product with the amine has been observed.

The patent application DE-A 35 11 273 describes the direct cyclization of α-formyl-β-formylaminopropionitrile sodium salt with acetamidine hydrochloride with neither having to derivatize any of the mentioned starting materials nor having to liberate the acetamidine from its hydrochloride:

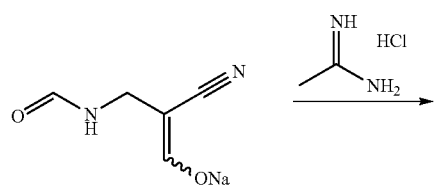

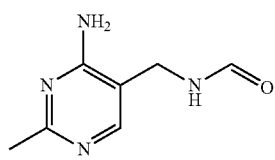

The process consists of reacting α-formyl-β-formylaminopropionitrile sodium salt having a minimal purity of 92% with acetamidine hydrochloride in a solvent like isopropanol, methylisobutylcarbinol, open chain- or cyclic ethers during 4 to 6 hours at reflux yielding 2-methyl-4-amino-5-formylaminomethylpyrimidine and subsequent hydrolysis leading to 4-amino-5-aminomethyl-2-methylpyrimidine. The reported yield is 57%. Unfortunately it was not possible to obtain the reported yield under the reported conditions. The highest yield obtainable under the reported conditions was in fact 35%.

Main disadvantages of the process described in the DE-A 35 11 273 for an industrial scale application are the poor yield—which makes the process economically unattractive—and the fact that the starting materials have to have a minimal purity of 92%. In addition to that, only the hydrochloride of the acetamidine can be used.

J. Heterocyclic Chem. 1982, 19, 493-496 describes the synthesis of 2-substituted 4-amino-6-methylpyrimidines by reacting e.g. propionitrile, benzonitrile or p-chlorobenzonitrile with 3-aminocrotononitrile in the presence of tetramethylammonium hydroxide penta-hydrate or potassium hydroxide.

It was therefore an object of the following invention to provide a new way to 4-amino-5-aminomethyl-2-alkylpyrimidine (compounds of formula V, especially 4-amino-5-aminomethyl-2-methylpyrimidine)

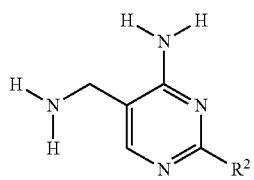

—which allows a considerable yield improvement and most preferred without using highly toxic reagents—like dimethylsulfate or o-chloro aniline.

DETAILED DESCRIPTION

Figure 1:
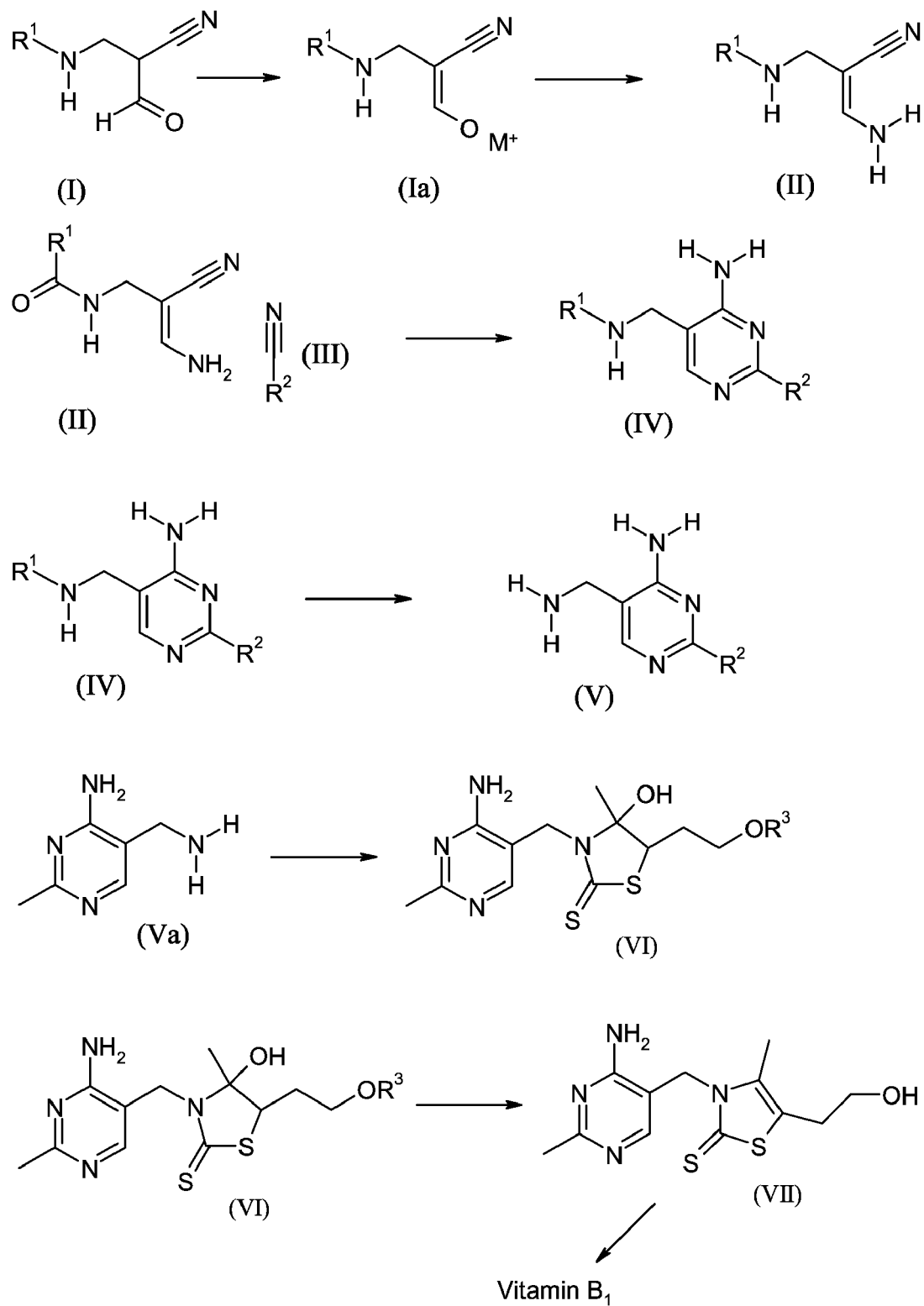
FIG. 1 is an overall reaction scheme starting with a compound of formula I to vitamin B1.
Figure 2:
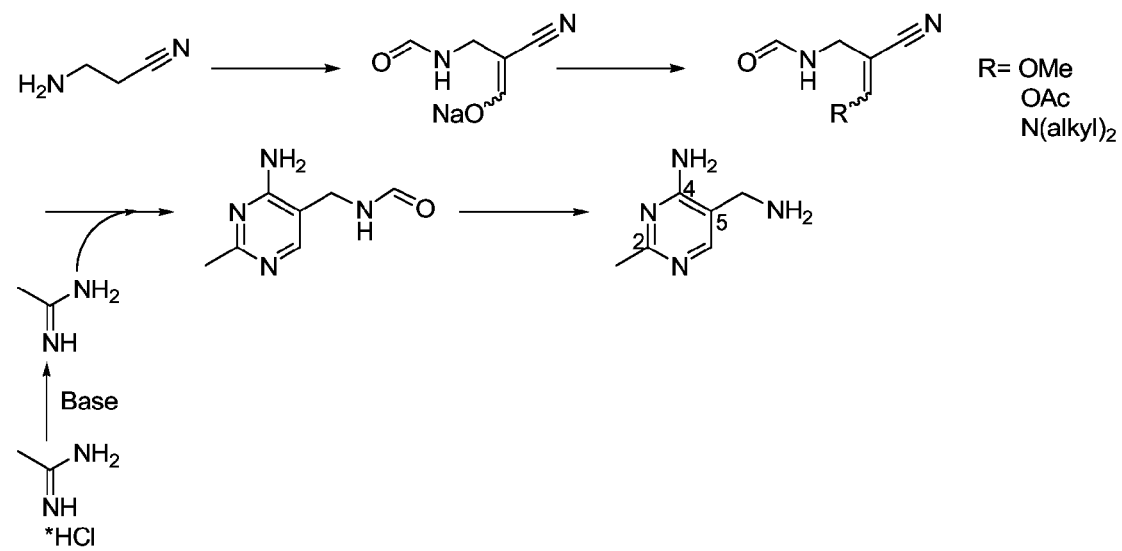
FIG. 2 is a reaction scheme showing the use of aminopropionitrile (APN) as a starting material.

The present invention is directed to a process for the manufacture of compounds of formula IV:

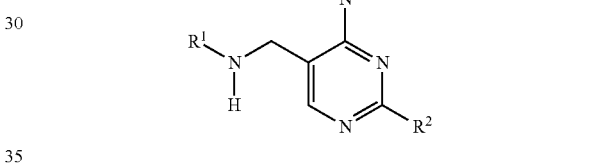

wherein $R^1$ is an amino protecting group, and $R^2$ is hydrogen or $C_{1-10}$ alkyl, comprising a) reacting a compound of formula Ia, wherein $M^+$ is a cation,

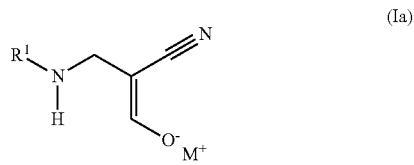

with an ammonium salt $NH_4^+X^-$, wherein $X^-$ is an anion, in a solvent to a compound of formula II;

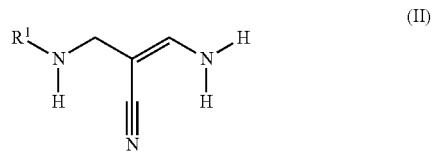

b) reacting a compound of formula II with a nitrile $R^2$—CN (compound of formula III) in the presence of a base to a compound of formula IV.

$R^1$ is an amino protecting group. Such groups are known to the person skilled in the art. Examples of such a group are Boc (=tert-butoxycarbonyl), Cbz (=benzyloxycarbonyl), allyloxy, benzyl and $CH_2C_6H_2(OMe)_3$ (trimethoxyphenylmethylene), as well as amides ($R^1$=C(O)$R^4$ with $R^4$ being hydrogen or straight- or branched-chain $C_{1-4}$ alkyl). Substituent $R^4$ is preferably hydrogen, methyl, ethyl, n-propyl or n-butyl, more preferably $R^4$ is hydrogen or methyl; most preferably $R^4$ is hydrogen.

Preferably $R^1$ is formyl or acetyl, more preferably $R^1$ is formyl.

Concerning $R^2$: the alkyl may be straight- or branched-chain or cyclic, preferably the $C_{1-10}$ alkyl is linear ($C_{1-10}$ alkyl) or branched ($C_{3-10}$ alkyl). Preferably $R^2$ is methyl, ethyl, propyl, isopropyl or isoprenyl; preferably $R^2$ is methyl, isopropyl or isoprenyl, more preferably $R^2$ is methyl.

The cation $M^+$ is preferably selected from the group consisting of $Li^+$, $Na^+$, $H^+$, $½ Mg^{2+}$ and $½ Zn^{2+}$.

The compound of formula Ia may be prepared by any method known to the person skilled in the art, such as by the synthesis of aminopropionitrile from the addition of ammonia to acrylonitrile, followed by formylation with methyl formate and sodium methoxide, as described in EP-A 205 131 and DE-A 2323845.

The anion $X^-$ is preferably selected from the group consisting of chloride, bromide, sulfate, acetate, oxalate, $HPO_4^{2-}$, more preferably $X^-$ is chloride, i.e. that ammonium chloride is reacted with a compound of formula Ia to a compound of formula II.

Step a)

The solvent in which step a) may be performed is not critical. Suitable solvents are e.g. alcohols such as methanol, 2-propanol and 1-butanol, aromatic hydrocarbons such as toluene, esters such as ethyl acetate, ethers such as diethyl ether and tetrahydrofuran, nitriles such as acetonitrile. The amount of the solvent is not critical either. The reaction is in general carried out in a suspension of the enolate Ia in the solvent, whereby the concentration of the starting enolate is in the range of from 10 to 50 weight-%, based on the total weight of the suspension.

Preferably the nitrile $R^2$—C≡N used in step b), e.g. acetonitrile, is used as solvent. For the preparation of vitamin $B^1$ it is preferred to use acetonitrile as solvent.

An example of a preferred mixture of solvents is a mixture of 2-propanol and toluene in a volume ratio of from 100:0 to 0:100, preferred in a volume ratio of from (80 to 50):(20 to 50), especially preferred in a volume ratio of from 65 to 35.

The temperature at which the reaction is performed should not exceed 120° C., as the enolate starts to decompose above 120° C. If the decomposition temperature of the enolate is lower, the reaction temperature has to be decreased accordingly. The preferred temperature is in the range of from 60 to 90° C., more preferably in the range of from 70 to 85° C.

The reaction may be performed at atmospheric pressure, as well as under a pressure of 5 bar $N_2$ or under a pressure of 5 bar $NH_3$.

The molar ratio of the starting materials, i.e. the molar ratio of the ammonium salt $NH_4^+X^-$ to the enolate of formula Ia may vary within a range of from 0.9:1 to 2.4:1. The best result was obtained with a molar ratio of $NH_4^+X^-$ to the enolate Ia of 1.3:1.

The produced water does not have to be removed to achieve total turnover.

The duration of the reaction is in the range of from 30 minutes to 20 hours, preferably in the range of from 3 to 7 hours, depending on the amount of starting materials.

The starting materials can be added in any order to the reaction vessel.

According to the present invention it is advantageous to adjust the reaction conditions of step a) as follows:

a reaction temperature in the range of from 40 to 120 C, preferred of from 60 to 90 C, more preferred of from 70 to 85 C a pressure in the range of from 1 to 5 bar, preferred of from 1 to 2 bar;

a reaction time in the range of from 0.5 to 20 hours, preferred of from 2 to 10 hours, more preferred of from 3 to 7 hours; most preferred of from 3 to 5 hours;

under protective atmosphere.

Step b)

The compound of formula II may be successfully employed in purity in the range of from 75 to 99%.

If the compound of formula IV is used to synthesize Grewe diamine acetonitrile (i.e. $R^2$=methyl) is used, in case of amprolium propionitrile (i.e. $R^2$=propyl) is used.

Advantageously the nitrile has already been used as solvent in step a). Thus, there is no need to remove the solvent, in which step a) has been performed, which means that after having performed step a) only a base has to be added.

As base any base known to the person skilled in the art may be used. In general bases, where the corresponding acids have a pKa of >9 should be suitable. Examples of suitable bases are hydroxides such as alkali metal hydroxides (esp. potassium and/or sodium hydroxide) and pseudo-alkali metal hydroxides, alkali metal hydrides like NaH and alcoholates such a sodium methanolate and potassium tert-butanolate. The hydroxides may be used in solid form as well as an alcoholic solution. Aqueous solutions of hydroxides may also be possible meaning that a certain amount of water is tolerated by the reaction system. Only a water content of ≧10 weight-%, based on the total weight of the reaction system, has to be avoided.

If the nitrile also serves as solvent, it may be used in excess compared to the compound of formula II. Otherwise it may be used in stoichiometric amounts to the compound of formula II. Preferably the nitrile is used in at least 1.5 mol equivalents compared to the compound of formula II.

The base may be used in catalytic amounts. Usually up to 1 equivalent (preferably from 0.01-1 equivalent) compared to the compound of formula II are used. Preferably ca. 0.2 mol %, based on the amount of the compound II are used.

Step b) may be performed at a temperature in the range of from 30 to 120° C., more preferably step b) may be performed at a temperature in the range of from 35 to 60° C., even more preferably step b) may be performed at a temperature in the range of from 40 to 50° C., most preferably step b) may be performed at a temperature in the range of from 40 to 45° C. (optimal temperature: 42° C.).

The starting materials can be added in any order to the reaction vessel.

According to the present invention it is advantageous to adjust the reaction conditions of step b) as follows:

a reaction temperature in the range of from 10 to 120 C, preferred of from 20 to 85 C, more preferred of from 40 to 45 C a pressure in the range of from 0.5 to 5 bar, preferred of from 1 to 3 bar;

a reaction time in the range of from 0.5 to 20 hours, preferred of from 2 to 18 hours, more preferred of from 7 to 15 hours;

under protective atmosphere.

The compounds of formula II, especially wherein $R^1$ is formyl, acetyl or tert-butoxy-carbonyl, are novel and have not been characterized until now. Preferred are the compounds of formula II, wherein $R^1$ is formyl and acetyl, more preferred is the compound of formula II, wherein $R^1$ is formyl.

Thus, the present invention is directed to trans-N-(3-amino-2-cyanoallyl)formamide, to cis-N-(3-amino-2-cyanoallyl)formamide and any mixture thereof, as well as to trans-N-(3-amino-2-cyanoallyl)acetamide, to cis-N-(3-amino-2-cyanoallyl)acetamide and any mixture thereof, and also to the compounds of formulae IIa (trans-1-N(tert-butoxycarbonyl)-3-amino-2-cyanoallylamin), IIb (cis-1-N(tert-butoxycarbonyl)-3-amino-2-cyanoallylamin) and IIc (any mixture of compounds of formulae IIa and IIb).

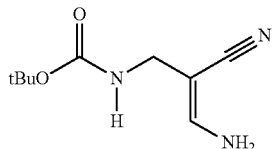
(IIa)

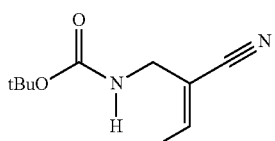
(IIb)

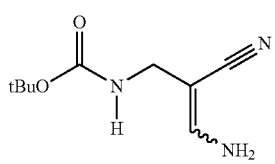
(IIc)

Since the compounds of formula II (especially with $R^1$=formyl, acetyl or tert-butoxy-carbonyl) are novel, a process for their preparation is also novel. Thus, the present invention is also directed to a process for the manufacture of compounds of formula II

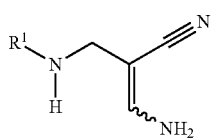
(II)

wherein $R^1$ is an amino protecting group (as defined and with the preferences as given above), comprising the step of reacting a compound of formula Ia, wherein $M^+$ is a cation (as defined and with the preferences as given above)

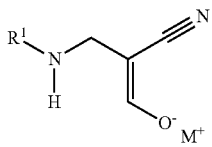
(Ia)

with an ammonium salt $NH_4^+X^-$, wherein $X^-$ is an anion (as defined and with the preferences as given above) in a solvent (as defined and with the preferences as given above) to a compound of formula II.

The preferences and preferred conditions for this reaction have already been disclosed above.

Another embodiment of the present invention is the use of a compound of formula IVa,

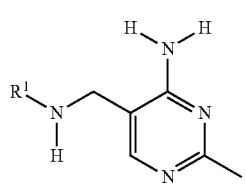
(IVa)

wherein $R^1$ is an amino protecting group, and $R^2$ is methyl, preferably obtained according to a process of the present invention, as intermediate in a process for the preparation of vitamin $B_1$.

A further object of the present invention is the use of a compound of formula II,

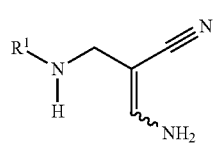
(II)

wherein $R^1$ is an amino protecting group (as defined and with the preferences as given above), preferably obtained according to a process of the present invention, as intermediate in a process for the preparation of vitamin $B_1$.

Moreover, an embodiment of the present invention is a process for the manufacture of Grewe diamine (GDA; 5-aminomethyl-2-methyl-pyrimidine-4-yl-amine), wherein from a compound of formula IVa the amino protecting group $R^1$ is removed.

The present invention encompasses also a process for the manufacture of Grewe diamine, wherein a compound of formula IV, wherein $R^1$=formyl or acetyl; and $R^2$=methyl, is hydrolysed. The hydrolysis may be carried out in the presence of bases such as hydroxides and ion exchangers as e.g. described in WO 2007/104 442; WO 2006/079 504 and DE-A 35 11 273.

The thus obtained GDA may, e.g., be further reacted with carbon disulfide and 3-chloro-5-acetoxypentan-2-one or another chloroketone derivate such as 3-chloro-5-hydroxypentan-2-one, 3-mercapto-5-hydroxypentan-2-one or 3-mercapto-5-acetoxypentan-2-one or any mixture thereof to form the compound of formula VI

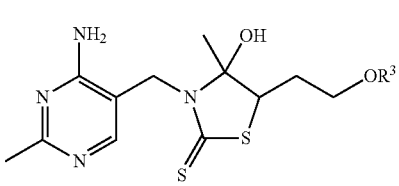
(VI)

with $R^3$ being $C_{1-4}$-alkanoyl, preferably acetyl (see e.g. G. Moine and H-P. Hohmann in Ullmann's Encyclopedia of Industrial Chemistry, VCH, Vol. A 27, 1996, 515-517 and the references cited therein).

Therefore, such a process for the manufacture of a compound of the formula VI is also a part of the present invention.

The compound of formula VI may then further be reacted with an acid to form the compound of formula VII

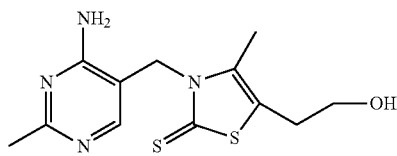
(VII)

(see e.g. G. Moine and H-P. Hohmann in Ullmann's Encyclopedia of Industrial Chemistry, VCH, Vol. A 27, 1996, 515-517 and the references cited therein).

Therefore, such a process for the manufacture of a compound of formula VII is also a part of the present invention.

The compound of the formula VII may then further be oxidized, preferably with $H_2O_2$, to vitamin $B_1$ of formula VIII

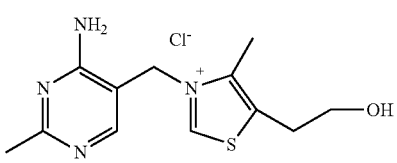
(VIII)

(see e.g. G. Moine and H-P. Hohmann in Ullmann's Encyclopedia of Industrial Chemistry, VCH, Vol. A 27, 1996, 515-517 and the references cited therein).

Therefore, the present invention comprises a process for the manufacture of vitamin $B_1$ wherein from a compound of formula IVa

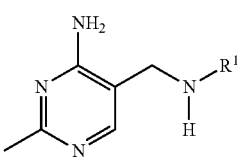
(IVa)

the amino protecting group $R^1$ is removed to obtain Grewe diamine, the thus obtained Grewe diamine is further reacted to a compound of formula VII,

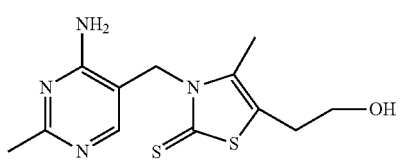
VII preferably as described above in more detail, and the thus obtained compound of formula VII is further oxidized, preferably with $H_2O_2$, to yield vitamin B1.

Preferably $R^1$ in formula IV is $C(O)R^4$ with $R^4$ being hydrogen or straight- or branched-chain $C_{1-4}$ alkyl (compound of formula IVa),

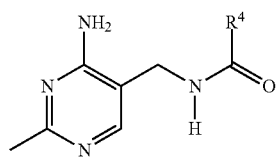
(IVa)

so that the group $C(O)R^4$ is hydrolysed to obtain Grewe diamine as described e.g. in the references cited above.

The overall reaction scheme starting with a compound of formula I to vitamin B1 is shown in FIG. 1.

The present invention comprises also the use of a compound of formula IVa obtained according to the process of the present invention as described above as intermediate in a process for the manufacture of vitamin B1.

Finally the present invention comprises the use of GDA obtained as described above as intermediate in a process for the manufacture of vitamin B1.

The invention will now be illustrated in the following non-limiting examples.

EXAMPLES

Example 1

Preparation of the enamine from α-formyl-β-formylaminopropionitrile sodium salt

Equipment: 1000 ml Two-necked round bottom flask, Argon supply, mechanical stirrer, oil heating bath 100.0 g of α-formyl-β-formylaminopropionitrile sodium salt (88% purity) and 37.3 g of ammoniumchloride were suspended in 500 ml of a mixture of isopropanol: toluene (65:35 Vol %) and heated to 130° C. bath temperature. The mixture was refluxed for 3 hours while stirring slowly (50 revolutions per minute). The mixture was allowed to cool to 25° C. after the three hours. The suspension was filtrated over a P3 Glass filter and washed with MeOH. The solvent was evaporated under reduced pressure (40° C. bath temperature, 50 mbar). A yellowish viscoseous oil was obtained. Yield: Filtrate 71.52 g (purity 75.6%): 75%.

Purification 30 g of the crude product were purified over 400 g $SiO_2$. The substance was therefore absorbed on hydromatrix with 7 L of a mixture of methanol (MeOH): methylenechloride ($CH_2Cl_2$) (1:9; Vol %) and a flow of 150 mL/min at 13 bar. In the end 20 g of product (purity of 90%) were obtained.

Spectroscopic Characterization:

$^1$H-NMR, DMSO-d6, δ in ppm: Z isomer δ=3.65 (d, J=5.65 Hz, 2H, CH$_2$); 6.45 (d, $^3$J=11.11 Hz, 2H, NH$_2$); 6.86 (t, $^3$J=11.11 Hz, 1H, C=CH); 7.98 (d, J=1.69 Hz, 1H, HCO), 8.15 (m, 1H, NH). E isomer: δ=3.72 (d, J=6.03 Hz, 2H, CH$_2$); 6.62 (d, J=10.7 Hz, 2H, NH$_2$), 6.94 (t, J=10.7, 1H, C=CH), 8.03 (d, J=1.69 Hz, 1H, HCO), 8.35 (m, 1H, NH).

$^{13}$C-NMR, DMSO-d6, δ in ppm: E isomer: δ=32.9, 73.8, 123.5, 148.9, 161.4.

Z isomer: 37.6, 71.8, 119.9, 150.8, 160.8.

MS (Electron Impact): M$^+$ 269 (bis-trimethylsilane adduct).

Examples 2-8

Example 1 was repeated applying the same protocol, but the solvent and the reaction time were different. The reaction temperature was the reflux-temperature of the corresponding solvent.

| Example | Solvent | Reaction Time [hours] | Yield [%] | Purity [%] |
|---|---|---|---|---|
| 2 | Methanol | 7 | 75 | 71 |
| 3 | Toluol | 7 | 68 | 65 |
| 4 | Isopropanol | 7 | 78 | 65 |
| 5 | 1-Butanol | 3 | 60 | 49 |
| 6 | Acetonitrile | 3 | 46 | 42 |

Example 1 was repeated applying the same protocol, but the amount of NH$_4$Cl was changed.

| Example | mol % NH$_4$Cl | Yield [%] | Purity [%] |
|---|---|---|---|
| 7 | 1 | 67 | 72 |
| 8 | 2.4 | 71 | 62 |

Example 9

Reaction of N-(3-amino-2-cyanoallyl)formamide with acetonitrile to N-formyl Grewe Diamine

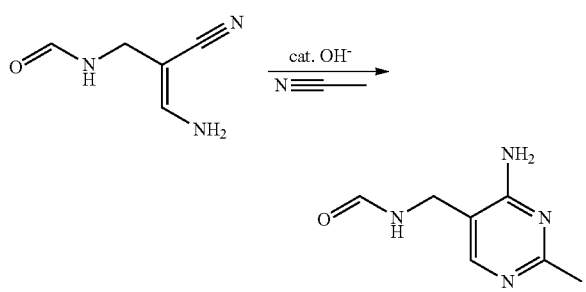

Equipment:
20 mL two-necked flask, fitted with a magnetic stirrer, a thermometer, a reflux condenser, and an argon supply.
Preparation:
250 mg of N-(3-amino-2-cyanoallyl)formamide were dissolved in 7.5 mL of acetonitrile and 74.8 mg of tetramethyl ammonium hydroxide pentahydrate were added. The solution was stirred for 16 hours at 42° C. Then the solvent was evaporated. The yield of N-formyl Grewe diamine was 58% based on converted enamine (80% conversion).

Example 9 was repeated applying the same protocol, but the temperature was changed.

| Example | Temperature | Yield [%] |
|---|---|---|
| 10 | 120° C. | 29 |
| 11 | 82° C. | 27.4 |
| 12 | 40° C. | 58 |

Example 9 was repeated applying the same protocol, but the temperature and the base was changed.

| Example | Base | Amount [mol %] | Temperature | Yield [%] |
|---|---|---|---|---|
| 13 | NaOCH$_3$ | 0.2 | 82° C. | 13.8 |
| 14 | (CH$_3$)$_3$COK | 0.2 | 82° C. | 20 |
| 15 | KOH | 0.2 | 82° C. | 15 |

The invention claimed is:

1. A process for the manufacture of compounds of formula IV:

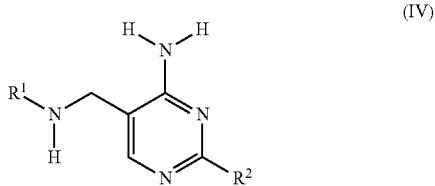

wherein R$^1$ is an amino protecting group, and R$^2$ is hydrogen or, C$_{1-10}$ alkyl, or isoprenyl, the process comprising:
a) reacting a compound of formula Ia:

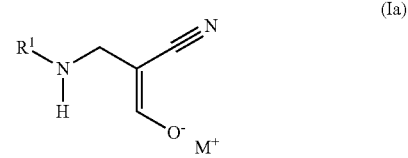

wherein M$^+$ is a cation with an ammonium salt NH$_4^+$X$^-$, wherein X$^-$ is an anion, in a solvent to obtain a compound of formula II:

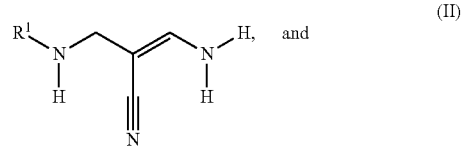

b) reacting a compound of formula II with a nitrile R$^2$—CN in the presence of a base to obtain a compound of formula IV.

2. The process according to claim 1, wherein R$^1$ is formyl or acetyl.

3. The process according to claim 1, wherein R$^2$ is methyl, ethyl, propyl, isopropyl or isoprenyl.

* * * * *